(12) United States Patent
Havelund

(10) Patent No.: US 6,310,038 B1
(45) Date of Patent: *Oct. 30, 2001

(54) PULMONARY INSULIN CRYSTALS

(75) Inventor: Svend Havelund, Bagsvaerd (DK)

(73) Assignee: Novo Nordisk A/S, Bagsvaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/045,038

(22) Filed: Mar. 20, 1998

Related U.S. Application Data

(60) Provisional application No. 60/041,390, filed on Mar. 27, 1997.

(30) Foreign Application Priority Data

Mar. 20, 1997 (DK) .................................................. 0317/97

(51) Int. Cl.$^7$ ........................... A61K 38/28; C07K 14/62
(52) U.S. Cl. ................................... 514/4; 514/3; 530/303; 530/305
(58) Field of Search .................................. 530/303, 304, 530/305; 514/3.4

(56) References Cited

U.S. PATENT DOCUMENTS

| | | | | |
|---|---|---|---|---|
| 3,719,655 | * | 3/1973 | Jackson ................................. | 530/305 |
| 4,639,332 | * | 1/1987 | Grau ..................................... | 530/303 |
| 5,506,203 | * | 4/1996 | Backstrom et al. .................... | 514/4 |
| 5,547,930 | * | 8/1996 | Balschmidt ............................ | 514/3 |
| 5,700,904 | * | 12/1997 | Baker et al. ........................... | 530/305 |
| 5,750,497 | * | 5/1998 | Havelund et al. ...................... | 514/3 |
| 5,898,028 | * | 4/1999 | Jensen et al. ........................... | 514/4 |
| 5,898,067 | * | 4/1999 | Balschmidt et al. .................... | 530/305 |

FOREIGN PATENT DOCUMENTS

| | | | |
|---|---|---|---|
| 709395 | * | 5/1996 | (EP) . |
| 94926816.3 | | 6/1996 | (EP) . |
| 95/07931 | * | 3/1995 | (WO) . |
| 95/24183 | * | 9/1995 | (WO) . |

OTHER PUBLICATIONS

Copy of Provisional Application 60/038,458, Feb. 20, 1997.*

Copy of Provisional Application 60/041,648, Mar. 27, 1997.*

R.K. Wolff, Ph.D., *Journal of Aerosol Medicine*, vol. 11, No. 4, pp. 197–219 (1998).

Patton et al., Advanced Drug Delivery Reviews, vol. 35, pp. 235–247(1999).

Sayani, Critical Reviews, vol. 13, No. 1 and 2 (1996), pp. 85,86,92–94, 96–102, 108–111, 116–117, 136–139.

Danielsen et al., Chapman & Hall, London, ISBN 0 412 48610 5, vol. 43, pp. 571–584 (1994).

Niven, Critical Reviews in Therapeutic Drug Carrier Systems, vol. 12, No. 2 and 3, pp. 151–231 (1995).

* cited by examiner

*Primary Examiner*—Jeffrey E. Russel
(74) *Attorney, Agent, or Firm*—Reza Green, Esq.

(57) ABSTRACT

The present invention relates to zinc free insulin crystals having a diameter below 10 $\mu$m and to therapeutic powder formulations suitable for pulmonary administration containing such insulin crystals. The crystals of the present invention exhibit a better stability profile than powders of essentially the same composition prepared by spray drying, freeze-drying, vacuum drying and open drying. The therapeutic powder formulations elucidate better flowing properties than corresponding amorphous powder formulations.

18 Claims, 1 Drawing Sheet

Photomicrography of the crystals obtained in example 1. The length the bar represents 10 μm.

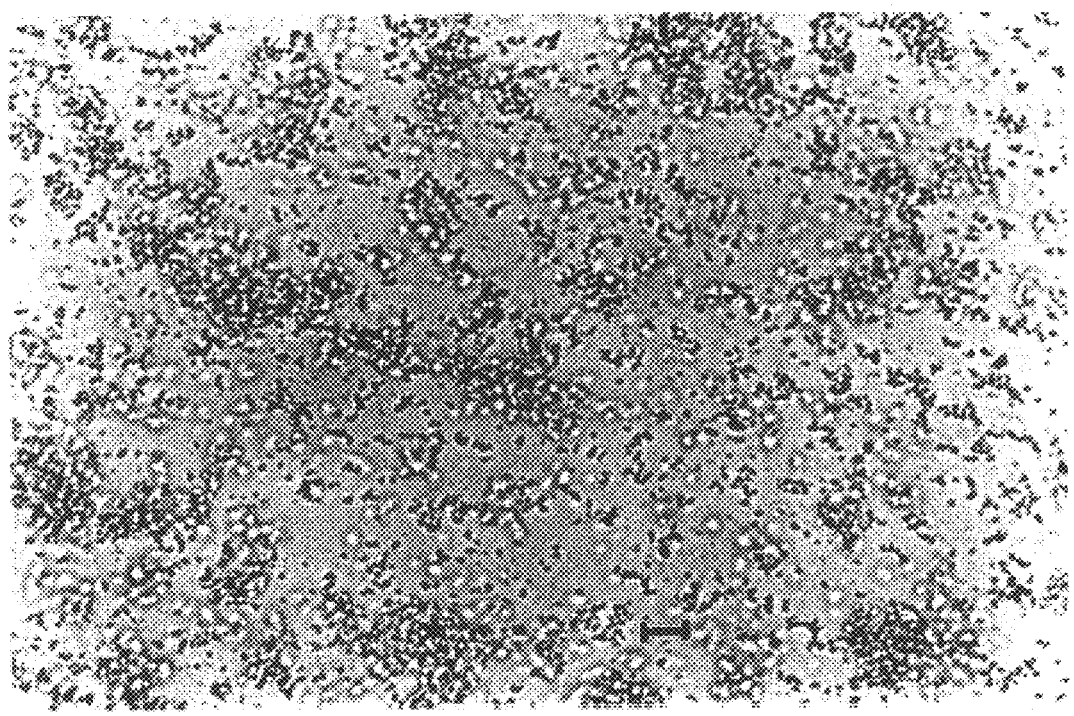
Fig. 1 Photomicrography of the crystals obtained in example 1. The length the bar represents 10 μm.

PULMONARY INSULIN CRYSTALS

CROSS-REFERENCE TO RELATED APPLICATIONS

This application claims priority of provisional application serial no. 60/041,390 filed Mar. 27, 1997 and Danish application serial no. 0317/97 filed Mar. 20, 1997, the contents of which are fully incorporated herein by reference.

FIELD OF THE INVENTION

The present invention relates to zinc free insulin crystals having a diameter below 10 μm and to therapeutic powder formulations suitable for pulmonary administration comprising such insulin crystals.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycemia levels, diabetic patients often practice multiple injection therapy, whereby insulin is administered with each meal.

Insulin is usually administrated by s.c. or i.m. injections. However, due to the adherent discomfort of injections alternative ways of administration such as nasal and pulmonary has been extensively investigated. For a review on alternative routes of administration of insulin, see Danielsen et al. New routes and means of insulin delivery, in: Childhood and Adolescent Diabetes (Ed. Kelnar), Chapman & Hall Medical, London 1994, pp. 571–584.

In order to circumvent injections, administration of insulin via the pulmonary route could be an alternative way to provide absorption profiles which mimic the endogenous insulin without the need to inject the insulin.

DESCRIPTION OF THE BACKGROUND ART

Administration of insulin via the pulmonary route can be accomplished by either an aqueous solution or a powder preparation. A description of the details can be found in several references, one of the latest being by Niven, Crit. Rev. Ther. Drug Carrier Sys, 12(2&3):151–231 (1995). One aspect covered in said review is the stability issue of protein formulations, aqueous solutions being less stable than powder formulation. So far, all powder formulations have been described as mainly amorphous.

A review of the permeation enhancers useful for the promotion of trans-mucosal absorption is found in Sayani et al., Crit. Rev. Ther. Drug Carrier Sys, 13(1&2): 85–184 (1996).

Patton et al., Inhale Therapeutic Systems, PCT WO 95/24183, claim a method for aerosolising a dose of insulin comprising providing the insulin as a dry powder dispersing an amount of the dry powder in a gas stream to form an aerosol capturing the aerosol in a chamber for subsequent inhalation.

It has been found that when insulin is combined with an appropriate absorption enhancer and is introduced into the lower respiratory tract in the form of a powder of appropriate particle size, it readily enters the systemic circulation by absorption through the layer of epithelial cells in the lower respiratory tract as described in U.S. Pat. No. 5,506,203. The manufacturing process described in said patent, comprising dissolution of insulin at acid pH followed by a pH adjustment to pH 7.4 and addition of sodium taurocholate before drying the solution by vacuum concentration, open drying, spray drying, or freeze drying, results in a powder composed of human insulin and absorption enhancer. The powder is characterized as mainly amorphous determined under a polarized light microscope. The desired particle size distribution is achieved by micronizing in a suitable mill, such as a jet mill, and the components may be mixed before or after micronizing. The biological effect of the powder obtained according to the methods described in this patent is only seen in the presence of a substantial amount of enhancer.

Platz et al., Inhale Therapeutic Systems, PCT WO 96/32149, describes spray drying of zinc insulin from a solution containing mannitol and a citrate buffer, pH 6.7. The inlet temperature is 120 to 122° C., the outlet temperature 80–81° C. The mass median aerodynamic diameter, MMAd, of the obtained insulin particles was determined to 1.3 to 1.5 μm.

In his thesis, "Insulin Crystals", Munksgaard Publisher 1958, p. 54–55, Schlichtkrull describes crystallization of zinc free, recrystallized porcine insulin from a solution comprising 0.01 M sodium acetate and 0.7%~0.12 M sodium chloride and 0.1% methylparahydroxybenzoate and using a pH of 7.0. The crystals obtained were 10–50 μm rhombic dodecahedral crystals showing no birefringence.

Jackson, U.S. Pat. No. 3,719,655 describes a method of purification of crude porcine and bovine insulin by crystallization. Zinc free crystals of insulin are obtained by crystallization at pH 8.2 (range 7.2–10) in the presence of 0.5 M (range 0.2 M–1 M) of a sodium, potassium, lithium or ammonium salt. Crystallization is achieved by addition of 1 N alkali metal hydroxide or 1 N ammonia to a solution of crude insulin in 0.5 N acetic acid to a pH of 8.2 is obtained. Alternatively, crystallization is achieved in an aqueous solution of impure insulin at pH 8.2 by addition of solid sodium chloride to a concentration of sodium ions of 0.45 M. The crystals appear in the octadecahedral or dodecahedral forms, i.e. crystals belonging to the cubic crystal system.

Baker et al., Lilly, EP 0 709 395 A2 (filed Oct. 31, 1994) describe a zinc free crystallization process for $LyS^{B28}$-$Pro^{B29}$ human insulin characterized by adjustment of the pH of a strongly buffered acid solution containing metal cations or ammonium ions and a preservative with metal hydroxide or ammonia to a value between 8.5 and 9.5.

The known methods for the manufacture of insulin particles of the desired size for pulmonary administration are cumbersome, generate problems with insulin dust and the investments in equipment are large. Furthermore, insulin is exposed to conditions where some denaturation is likely to take place. Thus WO 96/32149 discloses spray drying in a temperature range of 50° C. to 100° C., followed by milling of the particles to achieve to desired particle size.

Furthermore, the known powder formulations for pulmonary administration which have been described as mainly amorphous have a tendency to associate into aggregates in the dry powder.

DESCRIPTION OF THE INVENTION

Definitions

The expression "enhancer" as used herein refers to a substance enhancing the absorption of insulin, insulin analogue or insulin derivative through the layer of epithelial cells lining the alveoli of the lung into the adjacent pulmonary vasculature, i.e. the amount of insulin absorbed into the systemic system is higher than the amount absorbed in the absence of enhancer.

In the present context the expression "powder" refers to a collection of essentially dry particles, i.e. the moisture content being below about 10% by weight, preferably below 6 % by weight, and most preferably below 4% by weight.

The diameter of the crystals is defined as the Martin's diameter. It is measured as the length of the line, parallel to the ocular scale, that divides the randomly oriented crystals into two equal projected areas.

BRIEF DESCRIPTION OF THE INVENTION

It is an object of the present invention to provide an insulin powder suitable for pulmonary delivery which has a reduced tendency to associate into aggregates in the dry powder compared to the pulmonary insulin particles described in the prior art.

According to the present invention this object has been accomplished by providing zinc free insulin crystals having a diameter below 10 µm.

The crystals of the present invention furthermore exhibit a better stability profile than powders of essentially the same composition prepared by spray drying, freeze-drying, vacuum drying and open drying. This is probably due to the amorphous state of powders prepared by the other methods described. By this means it is possible to store the powder formulations based on the crystals of the present invention at room temperature in contrary to human insulin preparations for injections and some amorphous insulin powders without stabilizing agent which have to be stored between 2° C. to 8° C.

Furthermore, therapeutical powder formulations comprising the insulin crystals of the invention elucidates better flowing properties than corresponding amorphous powder formulations.

BRIEF DESCRIPTION OF THE FIGURES

FIG. 1 is a photomicrograph of crystals of human insulin.

PREFERRED EMBODIMENTS

The zinc free insulin crystals of the invention are advantageously provided in a crystal structure belonging to the cubic crystal system, preferably in the octadecahedral or dodecahedral crystal forms, since these crystal forms result in readily soluble product having excellent flowing properties.

The diameter of the insulin crystals is advantageously kept in the range of 0.2 to 5 µm, preferably in the range of 0.2 to 2 µm, more preferably in the range of 0.5 and 1 µm, to ensure high bioavailability and suitable profile of action, see PCT application No. WO 95/24183 and PCT application No. WO 96/32149.

In a preferred embodiment the insulin used is selected from the group consisting of human insulin, bovine insulin or porcine insulin, preferably human insulin.

In another preferred embodiment the insulin used is selected from the group consisting of rapid-acting insulins, preferably des(B30) human insulin, Asp$^{B28}$ human insulin or Lys$^{B28}$Pro$^{B29}$ human insulin.

In another preferred embodiment the insulin used is an insulin derivative, preferably selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$Pro$^{B29}$ human insulin, B28-N$^\epsilon$-palmitoyl Lys$^{B28}$Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamil)-des(B30) human insulin, B29-N$^\epsilon$-(ω-carboxyheptadecanoyl)des(B30) human insulin and B29-N$^\epsilon$-(ω-carboxyheptadecanoyl) human insulin, more preferably Lys$^{B29}$(N-ε acylated) des(B30) human insulin.

The insulin derivatives have a protracted onset of action and may thus compensate the very rapid increase in plasma insulin normally associated with pulmonary delivery. By carefully selecting the type of insulin, the present invention enables adjustment of the timing and to obtain the desired biological response within a defined time span.

In order to avoid irritation of the lungs and to eliminate immunological reactions, the employed insulin is preferably insulin which has been purified by chromatography, such as MC insulin (Novo), Single Peak insulin (E. Lilly) and RI insulin (Nordisk).

In a preferred embodiment the zinc free insulin crystals according to the invention further comprise a stabilizing amount of a phenolic compound, preferably m-cresol or phenol, or a mixture of these compounds.

The present invention is furthermore concerned with a therapeutic powder formulation suitable for pulmonary administration comprising the zinc free crystals described above.

In a preferred embodiment this therapeutic powder formulation further comprises an enhancer which enhances the absorption of insulin in the lower respiratory tract.

The enhancer is advantageously a surfactant, preferably selected from the group consisting of salts of fatty acids, bile salts or phospholipids, more preferably a bile salt.

Preferred fatty acids salts are salts of $C_{10-14}$ fatty acids, such as sodium caprate, sodium laurate and sodium myristate.

Lysophosphatidylcholine is a preferred phospholipid.

Preferred bile salts are salts of ursodeoxycholate, taurocholate, glycocholate and taurodihydrofusidate. Still more preferred are powder formulations according to the invention wherein the enhancer is a salt of taurocholate, preferably sodium taurocholate.

The molar ratio of insulin to enhancer in the powder formulation of the present invention is preferably 9:1 to 1:9, more preferably between 5:1 to 1:5, and still more preferably between 3:1 to 1:3.

The powder formulations of the present invention may optionally be combined with a carrier or excipient generally accepted as suitable for pulmonary administration. The purpose of adding a carrier or excipient may be as a bulking agent, stabilizing agent or an agent improving the flowing properties.

Suitable carrier agents include 1) carbohydrates, e.g. monosaccharides such as fructose, galactose, glucose, sorbose, and the like; 2) disaccharides, such as lactose, trehalose and the like; 3) polysaccharides, such as raffinose, maltodextrins, dextrans, and the like; 4) alditols, such as mannitol, xylitol, and the like; 5) inorganic salts, such as sodium chloride, and the like; 6) organic salts, such as sodium citrate, sodium ascorbate, and the like. A preferred group of carriers includes trehalose, raffinose, mannitol, sorbitol, xylitol, inositol, sucrose, sodium chloride and sodium citrate.

The crystals of the present invention are advantageously produced according to the following procedure:

a) providing a solution of insulin having a pH between 7.0 and 9.5;

b) mixing said solution with a solution of a salt of an alkali metal or an ammonium salt; and c) recovering the formed crystals.

The salt of an alkali metal or ammonium is preferably selected from the group consisting of the hydrochloride or acetate of sodium, potassium, lithium or ammonia, or mixtures thereof, more preferably sodium acetate.

In order to suppress the solubility of the crystals formed, the solution of insulin and/or the solution of a salt of an alkali metal or an ammonium salt preferably comprises a water miscible organic solvent in an amount which corresponds to 5 to 25% (v/v) in the solution obtained after mixing.

The water miscible organic solvent is preferably selected from the group consisting of ethanol, methanol, acetone and 2-propanol, more preferably ethanol.

A very uniform distribution of crystal sizes and crystals of the same crystallographic form are obtained when the two solutions are mixed within a period of less than 2 hours, preferably less than 1 hour, more preferably less than 15 minutes, still more preferably less than 5 minutes.

The crystallization process by which uniformly sized, small, zinc free crystals is obtained directly, without the use of milling, micronizing, sieving and other dust generating steps, is much to be preferred from the present state of the art in the manufacture of insulin powders for inhalation.

The concentration of insulin after mixing is preferably between 0.5% and 10%, more preferably between 0.5% and 5%, still more preferably between 0.5% and 2%.

The concentration of salt after mixing is preferably between 0.2 M and 2 M, more preferably about 1 M.

The method according to the present invention may further comprise a washing step, in which the crystals obtained are washed with a solution comprising auxiliary substances to be included in the final dry powder, preferably an enhancer and/or a carbohydrate, and optionally comprising 5–25% of an alcohol, preferably ethanol, 5–50 mM of a preservative preferably phenol, and 0.1–2 M of a salt such as sodium acetate.

This invention is further illustrated by the following examples which, however, are not to be construed as limiting.

EXAMPLE 1

Crystallization in 1 M sodium acetate.

2 g of highly purified human insulin is dissolved in 100 ml 10 mM tris buffer, pH 8.0 in 20% (v/v) of ethanol in water. To this solution is added 100 ml 2 M sodium acetate under stirring. A precipitate forms immediately. After 2 days at room temperature microscopy shows small crystals having a diameter between 0.5 and 1 $\mu$m. The crystals are collected by centrifugation at $-10°$ C., washed once with 20 ml ice cold 10% ethanol (v/v) in water, isolated by centrifugation and dried by lyophilization. The obtained crystals are shown in FIG. 1.

EXAMPLE 2

Crystallization in the presence of taurocholic acid sodium salt.

10 mg of human insulin and 5 mg of taurocholic acid sodium salt are dissolved in 500 $\mu$l 10 mM tris buffer, pH 8.0 in 20% (v/v) of ethanol in water. To this solution is added 500 $\mu$l 2 M sodium acetate. Microscopy after 1 hour and after 24 hours shows identically appearance of the crystals, i.e. uniformly sized crystals having diameters between 0.5 and 1 $\mu$m. The crystals were washed three times with 100 $\mu$l 10% (v/v) ethanol in water at $-10°$ C. and dried in vacuo. HPLC of the crystals showed that the washings had removed the taurocholic acid sodium salt from the insulin crystals.

EXAMPLE 3

Crystallization in the presence of Tween 80, bis(2-ethylhexyl) sulfosuccinate sodium salt, chitosan, L-$\alpha$-lysophosphatidylcholine myristoyl and polyoxyethylene sorbitan monolaurate.

Crystallization was performed as described in Example 2 except that taurocholic acid sodium salt was replaced by 0.6% (w/v) Tween 80, 0.56% (w/v) bis(2-ethylhexyl) sulfosuccinate sodium salt, 0.32% (w/v) chitosan, 0.52% (w/v) L-$\alpha$-lysophosphtidylcholine myristoyl, and 1% (w/v) polyoxyethylene sorbitan monolaurate, respectively. All five examples resulted in uniformly sized crystals having diameters between 0.5 and 1 $\mu$m.

EXAMPLE 4

Crystallization in 10% (v/v) ethanol.

Crystallization was performed in 10% (v/v) ethanol as described in Example 1, using 4 combinations of pH and concentration of sodium acetate:

4.1: pH 7.5 and 1 M sodium acetate 4.2: pH 7.5 and 1.5 M sodium acetate 4.3: pH 9.0 and 1 M sodium acetate 4.4: pH 9.0 and 1.5 M sodium acetate All 4 combinations yielded uniformly sized crystals having diameters between 0.5 and 1 $\mu$m.

EXAMPLE 5

Crystallization in 15% (v/v) ethanol.

Crystallization was performed in 15% (v/v) ethanol, using 6 combinations of pH and concentration of sodium acetate:

5.1: pH 7.5 and 1 M sodium acetate 5.2: pH 7.5 and 1.5 M sodium acetate 5.3: pH 7.5 and 2 M sodium acetate 5.4: pH 9.0 and 1 M sodium acetate 5.5: pH 9.0 and 1.5 M sodium acetate 5.6: pH 9.0 and 2 M sodium acetate All 6 combinations yielded uniformly sized crystals having diameters between 0.5 and 1 $\mu$m.

EXAMPLE 6

Crystallization in 20% (v/v) ethanol.

Crystallization was performed in 20% (v/v) ethanol using 4 combinations of pH and concentration of sodium acetate:

6.1: pH 7.5 and 1 M sodium acetate 6.2: pH 7.5 and 1.5 M sodium acetate 6.3: pH 7.5 and 2 M sodium acetate 6.4: pH 9.0 and 1 M sodium acetate All 4 combinations yielded uniformly sized crystals having diameters between 0.5 and 1 $\mu$m.

EXAMPLE 7

Crystallization at pH 7.5, 8.0, 8.5 and 9.0 in 20% ethanol (v/v) using slow addition of sodium acetate.

Crystallization was performed using solutions as described in Example 1, except that the 2 M sodium acetate was dissolved in 20% (v/v) ethanol in water. The pH of the insulin solutions were adjusted to 7.5, 8.0, 8.5 and 9.0, respectively. The sodium acetate solution was added in 12 aliquots over a period of 2 hours, using 10 min between additions. At all 4 pH values uniformly sized crystals having diameters between 0.5 and 1 µm were obtained.

EXAMPLE 8

Crystallization of $Lys^{B29}$(ε-myristoyl) des(B30) human insulin in the presence of taurocholic acid sodium salt.

10 mg of $Lys^{B29}$(ε-myristoyl) des(B30) human insulin and 5 mg of taurocholic acid sodium salt are dissolved in 500 µl 10 mM tris buffer, pH 8.0 in 20% (v/v) of ethanol in water. To this solution is added 500 µl 2 M sodium acetate. Microscopy after 1 hour and after 24 hours shows identically appearance of the crystals, i.e. uniformly sized crystals having diameters between 0.5 and 1 µm. The crystals were washed once with 300 µl 10% (v/v) ethanol in water at −10° C. and dried in vacuo. HPLC of the crystals showed that the washings had removed the taurocholic acid sodium salt from the crystals of $Lys^{B29}$(ε-myristoyl) des(B30) human insulin.

What is claimed is:

1. Zinc free insulin crystals having a diameter below 10 µm, wherein said insulin is selected from the group consisting of human insulin and $Lys^{B29}$(N-ε-acylated) des(B30) human insulin.

2. Zinc free insulin crystals according to claim 1 having a crystal structure belonging to the cubic crystal system.

3. Zinc free insulin crystals according to claim 2 in the octadecahedral or dodecahedral crystal forms.

4. Zinc free insulin crystals according to claim 1 having a diameter in the range of 0.2 to 5 µm.

5. Zinc free insulin crystals according to claim 1 further comprising a stabilizing amount of a phenolic compound.

6. Zinc free insulin crystals according to claim 5 comprising m-cresol or phenol, or a mixture thereof.

7. A therapeutic powder formulation suitable for pulmonary administration comprising the zinc free insulin crystals according to claim 1.

8. The therapeutic powder formulation according to claim 7 which further comprises an enhancer which enhances the absorption of insulin in the lower respiratory tract.

9. The therapeutic powder formulation according to claim 8 wherein the enhancer is a surfactant.

10. The therapeutic powder formulation according to claim 9 wherein the surfactant is a salt of a fatty acid, a bile salt or a phospholipid.

11. The therapeutic powder formulation according to claim 10 wherein the surfactant is a salt of taurocholate.

12. The therapeutic powder formulation according to claim 7 which further comprises a carrier, selected from the group consisting of trehalose, raffinose, mannitol, sorbitol, xylitol, inositol, sucrose, sodium chloride and sodium citrate.

13. A method for the preparation of zinc free insulin crystals having a diameter below 10 µm, comprising the steps of:
   a) providing a first solution of insulin having a pH between 7.0 and 9.5;
   b) mixing said first solution with a second solution of a salt of an alkali metal or an ammonium salt, wherein either or both of said first and second solutions comprises a water miscible organic solvent selected from the group consisting of ethanol, methanol, acetone and 2-propanol in an amount which provides a concentration of said organic solvent of 5 to 25% (v/v) in the solution obtained after mixing, and wherein the first and second solution are mixed within a period of less than 15 minutes; and
   c) recovering the formed crystals.

14. The method according to claim 13, wherein the salt of an alkali metal or ammonium is selected from the group consisting of the hydrochloride or acetate of sodium, potassium, lithium or ammonia, and mixtures thereof.

15. The method according to claim 13, wherein the concentration of insulin after mixing is between 0.5% and 10% by weight.

16. The method according to claim 13, wherein the concentration of salt after mixing is between 0.2 M and 2 M.

17. The method according to claim 13, which further comprises a washing step, in which the crystals obtained are washed with a solution which comprises auxiliary substances and optionally comprises 5–25% of an alcohol, 5–50 mM of a preservative, and 0.1–2 M of a salt.

18. A method of treating diabetes mellitus comprising administering to a person in need of such treatment an effective amount of a therapeutic powder formulation according to claim 7.

* * * * *